United States Patent [19]

Hanifin, Jr. et al.

[11] 4,092,311

[45] May 30, 1978

[54] HYPOTENSIVE ALKYL-3-[6-(ARYL)-3-PYRIDAZINYL]-CARBAZATES

[75] Inventors: John William Hanifin, Jr.; Daniel Bryan Moran, both of Suffern; Jay Donald Albright, Nanuet, all of N.Y.; George Rodger Allen, Jr., Old Tappan, N.J.

[73] Assignee: American Cyanamid Company, Stamford, Conn.

[21] Appl. No.: 827,403

[22] Filed: Aug. 24, 1977

Related U.S. Application Data

[63] Continuation of Ser. No. 692,254, Jun. 3, 1976, abandoned, which is a continuation-in-part of Ser. No. 552,024, Feb. 24, 1975, abandoned.

[51] Int. Cl.² ............... C07D 237/20; A61K 31/50

[52] U.S. Cl. .................. 544/224; 424/250; 544/239

[58] Field of Search .................. 260/250 A

[56] References Cited

U.S. PATENT DOCUMENTS 3,925,381  12/1975  Carpi et al. .................. 260/250 A

OTHER PUBLICATIONS

Basa et al. J. Chem. Soc 1963, 5660.
Mallett et al. J. Chem. Soc [c] 1966, 2038.

*Primary Examiner*—Donald G. Daus
*Assistant Examiner*—Mark L. Berch
*Attorney, Agent, or Firm*—Edward A. Conroy, Jr.

[57] ABSTRACT

This disclosure describes novel alkyl 3-[6-(aryl)-3-pyridazinyl]-carbazates useful as hypotensive agents in mammals.

11 Claims, No Drawings

HYPOTENSIVE ALKYL-3-[6-(ARYL)-3-PYRIDAZINYL]-CARBAZATES

CROSS REFERENCE TO RELATED APPLICATIONS

This application is a continuation of our copending application Ser. No. 692,254, filed June 3, 1976 now abandoned, which in turn is a continuation-in-part of our abandoned application Ser. No. 552,024, filed Feb. 24, 1975 now abandoned.

BACKGROUND OF THE INVENTION

This invention is concerned with novel alkyl 3-[6-(aryl)-3-pyridazinyl]carbazates useful as hypotensive agents. These compounds can be prepared from the 3-halo-6-arylpyridazines and 3-hydrazino-6-arylpyridazines. Belgian Pat. No. 811,847 describes compounds having hypotensive activity of the formula:

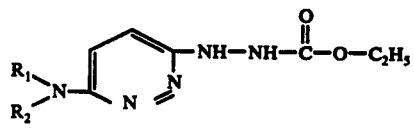

wherein $R_1$ and $R_2$ are alkyl ($C_1$–$C_6$), 2-hydroxyethyl or 2-hydroxypropyl. Herz and Kreislaufwirksame Pharmaka, W. Forster, et al. Editors (Barth, Leipzig), at page 282, (1968), disclose the compound p-anisylpyridazine-hydrazine. However, no art is known which discloses the alkyl 3-[6-(aryl)-3-pyridazinyl]carbazates disclosed and claimed herein or their utility as hypotensive agents.

BRIEF SUMMARY OF THE INVENTION

This invention discloses novel pyridazinyl carbazates of the formula:

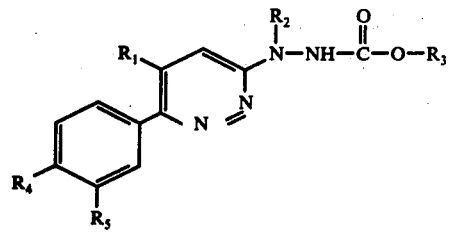

wherein $R_1$, $R_2$ and $R_3$ are each individually selected from the group consisting of hydrogen and lower alkyl ($C_1$–$C_4$); and $R_4$ and $R_5$ are each individually selected from the group consisting of hydrogen, chloro, cyano, bromo, fluoro, methoxy, nitro, amino, trifluoromethyl and carbamoyl with the proviso that at least one of $R_4$ and $R_5$ is hydrogen.

The invention is also concerned with a method of lowering blood pressure in mammals, specifically warm-blooded animals, by orally administering an effective amount of the above novel carbazates to said mammals, and with therapeutic compositions in unit dosage form containing said carbazates.

DETAILED DESCRIPTION OF THE INVENTION

The novel carbazates of the present invention are generally obtainable as white crystalline materials having characteristic melting points and absorption spectra and which may be purified by recrystallization from common solvents such as ethanol, methanol, acetone, and mixtures thereof. They are soluble in many organic solvent such as dimethylformamide, chloroform, and the like, but are relatively insoluble in nonpolar solvents such as hexane.

The novel carbazates (VI) of the present invention may be readily prepared from appropriately substituted 3-(aroyl)alkanoic acids (I) as set forth in the following reaction scheme:

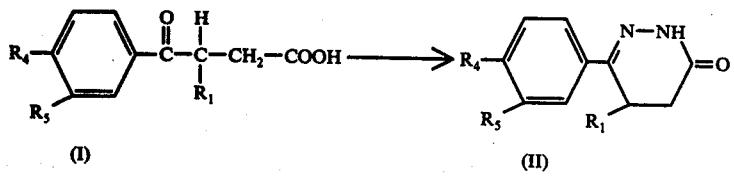

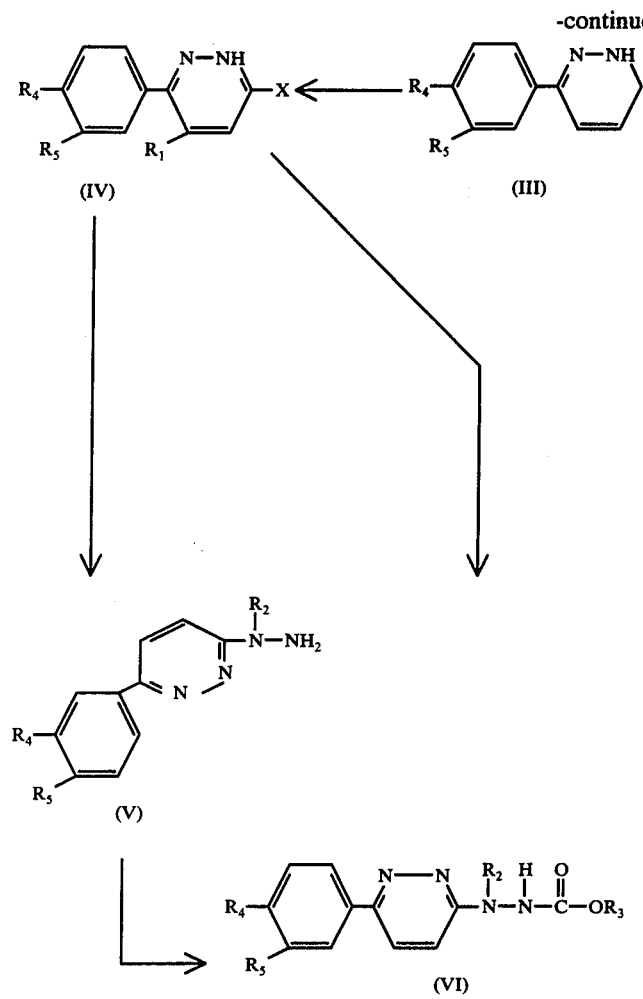

wherein $R_1$, $R_2$, $R_3$, $R_4$ and $R_5$ are as hereinabove defined.

In accordance with this reaction scheme a 3-(aroyl)alkanoic acid (I) is reacted with hydrazine to yield a 6-(aryl)-4,5-dihydro-3(2H)-pyridazinone (II). The condensation with hydrazine is carried out in a solvent such as ethanol, toluene, butanol, dioxane and the like for 1-5hours. Reaction of (II) with bromine in glacial acetic acid at 100° C results in bromination, immediately followed by dehydrobromination to yield the 6-(aryl)-3(2H)-pyridazinones (III). Alternatively the 6-(aryl)-4,5-dihydro-3(2H)-pyridazinones may be converted to 6-(aryl)-3(2H)-pyridazinones by dehydrogenation with catalysts, activated manganese dioxide or the sodium salt of m-nitrobenzenesulfonic acid. Reaction of (III) with phosphorus oxychloride gives the 6-(aryl)-3-halopyridazines (IV). Treatment of (IV) with a lower alkyl carbazate yields the novel lower alkyl 3-[6-(aryl)-3-pyridazinyl]carbazates (VI) of this invention. Treatment of (IV) with hydrazine or substituted hydrazine yield the 6-(aryl)-3-hydrazinopyridazines (V). Alternatively, the 3-[6-(aryl)-3-pyridazinyl]carbazates (VI) may be prepared from lower alkyl 6-(aryl)-3-hydrazinopyridazines (V) by reaction with lower alkyl chloroformates.

The reaction of o, m or p-nitrobenzoylpropionic acids with hydrazine gives the 6-(o, m or p-nitrophenyl)-4,5-dihydro-3(2H)-pyridazinones which may be dehydrogenated with bromine in glacial acetic acid to the 6-(o, m or p-nitrophenyl)-3(2H)-pyridazinones. Catalytic reduction then gives the 6-(o, m or p-aminophenyl)-3(2H)-pyridazinones which are useful intermediates in the preparation of the 6-(o, m or p-substituted phenyl)-3(2H)-pyridazinones.

For example, the intermediate cyano compounds for preparation of the novel compounds of this invention may be prepared by diazotization of an appropriately substituted 6-(o, m or p-aminophenyl)-3(2H)-pyridazinone and replacement of the diazonium group with a cyano group. Alternatively, the intermediate cyano compounds may be prepared by diazotization of an appropriately substituted 6-(o, m or p-aminophenyl)-4,5-dihydro-3(2H)-pyridazinone, followed by replacement of the diazonium group with a cyano group and dehydrogenation with bromine in glacial acetic acid.

The diazotization is preferably carried out by adding sodium nitrite to a solution of the amine in dilute hydrochloric acid at a temperature of 0°-5° C. An excess of mineral acid is used over and above the amount needed to form the salt of the amine and to decompose the sodium nitrite. The resulting diazonium salt is neutralized with a base such as sodium bicarbonate and added to a cold (10°-15° C.) aqueous solution of cuprous cyanide or potassium cyanide. After the addition the resulting mixture is stirred at room temperature for 10-20 hours and the desired cyano compound isolated.

Typical intermediate compounds for preparation of the novel carbazates of this invention which may be prepared by the above methods are, for example:

6-(o-cyanophenyl)-3(2H)-pyridazinone
6-(o-cyanophenyl)-5-methyl-3(2H)-pyridazinone
6-(m-cyanophenyl)-3(2H)-pyridazinone
6-(m-cyanophenyl)-5-methyl-3(2H)-pyridazinone
6-(p-cyanophenyl)-3(2H)-pyridazinone
6-(p-cyanophenyl)-5-methyl-3(2H)-pyridazinone
6-(p-cyanophenyl)-5-ethyl-3(2H)-pyridazinone
6-(m-cyanophenyl)-5-ethyl-3(2H)-pyridazinone
6-(p-cyanophenyl)-5-propyl-3(2H)-pyridazinone
6-(m-cyanophenyl)-5-propyl-3(2H)-pyridazinone The intermediate halogen substituted compounds may be prepared by diazotization of the appropriately substituted 6-(o, m or p-aminophenyl)-3(2H)-pyridazinones and replacement of the diazonium group with a halogen atom. Alternatively, the intermediate halogen substituted compounds may be prepared by diazotization of an appropriately substituted 6-(o, m or p-aminophenyl)-4,5-dihydro-3(2H)-pyridazone followed by replacement of the diazonium group with a halogen atom and dehydrogenation with bromine in glacial acetic acid.

Typical intermediate compounds for the preparation of the novel carbazates of this invention which may be prepared by the above methods are, for example:

6-(o-chlorophenyl)-3(2H)-pyridazinone
6-(m-chlorophenyl)-3(2H)-pyridazinone
6-(p-chlorophenyl)-3(2H)-pyridazinone
6-(o-bromophenyl)-3(2H)-pyridazinone
6-(m-bromophenyl)-3(2H)-pyridazinone
6-(p-bromophenyl)-3(2H)-pyridazinone
6-(m-fluorophenyl)-3(2H)-pyridazinone
6-(p-fluorophenyl)-3(2H)-pyridazinone
6-(p-chlorophenyl)-5-methyl-3(2H)-pyridazinone
6-(p-bromophenyl)-5-methyl-3(2H)-pyridazinone
6-(p-fluorophenyl)-5-methyl-3(2H)-pyridazinone
6-(p-chlorophenyl)-5-ethyl-3(2H)-pyridazinone
6-(m-bromophenyl)-5-methyl-3(2H)-pyridazinone The appropriately substituted 6-(o, m or p-bromophenyl)-3(2H)-pyridazinones may be converted to the 6-(o, m or p-cyanophenyl)-3(2H)-pyridazinones by reaction with cuprous cyanide. The displacement of the bromine group by cyanide is preferably carried out by refluxing in a polar solvent such as N,N-dimethylformamide for 3–10 hours.

The intermediate 6-(substituted aryl)-3(2H)-pyridazinones are obtained directly by reaction of the appropriately β-(substituted aroyl)alkanoic acids with hydrazine followed by dehydrogenation with bromine in glacial acetic acid or with the sodium salt of m-nitrobenzenesulfonic acid. Suitable β-(substituted aroyl)alkanoic acids contemplated for the preparation of the desired 6-(substituted aryl)-3(2H)-pyridazinones are 3-(o-nitrobenzoyl)propionic acid 3-(p-bromobenzoyl)butyric acid, 3-(p-chlorobenzoyl)butyric acid, 3-(p-fluorobenzoyl)butyric acid, 3-(m-nitrobenzoyl)butyric acid, 3-(benzoyl)butyric acid, 3-(p-fluorobenzoyl)pentanoic acid, 3-(benzoyl)propionic acid, 3-(p-bromobenzoyl)-2-methylbutyric acid, 3-(p-nitrobenzoyl)propionic acid, 3-(p-nitrobenzoyl)butyric acid and the like.

The intermediate 6-(aryl)-3(2H)-pyridazinones and the 6-(substituted phenyl)-3(2H)-pyridazinones when reacted with phosphorus oxychloride give 6-(aryl)-3-chloropyridazines and 6-(substituted phenyl)-3-chloropyridazines which on reaction with lower alkyl carbazates give the novel carbazates of the present invention.

The reaction of loweralkyl carbazates with 6-(substituted aryl)-3-chloropyridazines may be carried out in inert solvents such as lower alkanols, toluene, xylene, dioxane, N,N-dimethylformamide, N,N-dimethylacetamide and the like or without a solvent at elevated temperatures. The preferred method is the reaction of two moles of a lower alkyl carbazate with one mole of a 6-(substituted aryl)-3-chloropyridazine in refluxing n-butanol for 2–20 hours. Alternatively, one mole of a 6-(substituted aryl)-3-chloropyridazine and one mole of a lower alkyl carbazate may be reacted in an inert solvent in the presence of acid acceptors such as sodium or potassium bicarbonate, or N,N-diethylisopropylamine.

The novel carbazates of this invention may be prepared by first reacting the 6-(substituted aryl)-3-chlorpyridazine with hydrazine or substituted hydrazines such as methylhydrazine, and the like and then reacting the corresponding 6-(substituted aryl)-3-hydrazine derivatives thus obtained with a lower alkyl chloroformate.

The reaction of 6-(substituted aryl)-3-chloropyridazines with hydrazine and alkylhydrazines may be carried out in solvents such as lower alkanols, xylene, dioxane, tetrahydrofuran and the like or without solvent. The reaction of the 6-(substituted aryl)-3-hydrazinopyridazines with a lower alkyl chlorocarbonate may be carried out in ethanol, or inert solvents such as chloroform, tetrahydrofuran, dioxane, ether, benzene, xylene and the like with or without an acid acceptor such as N,N-diethylisopropylamine, alkali metal carbonates, or alkali metal bicarbonates.

Typical carbazates of the present invention which may be thus prepared are, for example, ethyl 3-[6-(p-cyanophenyl)-3-pyridazinyl]carbazate
ethyl 3-[6-(p-bromophenyl)-3-pyridazinyl]carbazate
ethyl 3-[6-(p-chlorophenyl)-3-pyridazinyl]carbazate
ethyl 3-[5-methyl-6-(m-nitrophenyl)-3-pyridazinyl]carbazate
ethyl 3-[6-(p-cyanophenyl)-5-methyl-3-pyridazinyl]carbazate
ethyl 3-[6-(p-bromophenyl)-5-methyl-3-pyridazinyl]carbazate
ethyl 3-[6-(m-aminophenyl)-5-methyl-3-pyridazinyl]carbazate
ethyl 3-[6-(p-aminophenyl)-5-methyl-3-pyridazinyl]carbazate
ethyl 3-[6-(p-methoxyphenyl)-3-pyridazinyl]carbazate
butyl 3-[6-(p-chlorophenyl)-3-pyridazinyl]carbazate
butyl 3-[6-(p-cyanophenyl)-5-methyl-3-pyridazinyl]carbazate
propyl 3-[6-(p-bromophenyl)-3-pyridazinyl]carbazate
methyl 3-[6-(p-methoxyphenyl)-3-pyridazinyl]carbazate
ethyl 3-[6-(p-fluorophenyl)-5-methyl-3-pyridazinyl]carbazate
t-butyl 3-[6-(p-cyanophenyl)-5-methyl-3-pyridazinyl]carbazate
t-butyl 3-[6-(m-nitrophenyl)-5-methyl-3-pyridazinyl]carbazate
ethyl 3-[6-(m-cyanophenyl)-5-methyl-3-pyridazinyl]carbazate The carbazates of the present invention show hypotensive activity when administered to mammals, specifically warm-blooded animals. Conscious, normotensive male albino Wistar strain rats averaging approximately 250 g. were fastened to rat boards in a supine position by means of canvas vests and limb ties. The femoral areas were anesthetized (subcutaneous infiltration of lidocaine), and the left or right common iliac arteries were exposed and clamped off proximally by an artery clamp and distally with thread. Incision were made near the tie and short nylon catheters were inserted and tied in place. The other end of the catheters were fitted with 24 gauge hubless needles attached to thick-walled polyethylene tubes. The test compounds were administered to the animals orally, by gavage (stomach tube). The test compounds were suspended or dissolved in 2% aqueous starch solution, one ml. of which gave, per 100 g. of body weight, the desired dose. Mean arterial blood pressure was measured 4 hours and 24 hours after administration of the compounds. Comparisons were then made to the mean control pressure of 122 mm of mercury, which is the average of a number of controls recorded over months of testing. Blood pressure measurements were made with four Statham P23 Db strain gauges (Statham Instruments, Inc., Los Angeles, Calif.), attached to a Beckman Dynograph Recorder equipped with four strain gauge preamplifiers with averaging circuits for measuring mean arterial pressure.

The results with representative compounds of the present invention appear in Table I.

of body weight is about 35 mg. to about 2.8 g. and preferably about 140 mg. to about 2.0 g.

For therapeutic administration, the active carbazates of this invention may be incorporated with excipients and used, for example, in the form of tablets, troches, capsules, elixirs, suspensions, syrups, wafers, and the like. Such compounds and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations according to the present invention are prepared so that a dosage unit form contains between about 20 and about 250 milligrams of active compound.

The tablets, troches, pills, capsules and the like may contain the following: a binder such as gum tragacanth, acacia, corn starch, or gelatin; a disintegrating agent such as corn starch, potato starch, alignic acid and the like; a lubricant such as magnesium stearate; and a sweetening agent such as sucrose or saccharin may be added or a flavoring agent such as peppermint, oil of wintergreen or cherry flavoring. A syrup or elixir may contain the active compounds, sucrose as a sweetening agent, methyl and propyl parabens as preservatives, a dye and a flavoring such as cherry or orange flavor.

Table I

| COMPOUND | DOSE (mg/Kg) | NO. OF RATS | MEAN ARTERIAL BLOOD PRESSURE (mm Hg) | |
|---|---|---|---|---|
| | | | 4 Hr. | 24 Hr. |
| Ethyl 3-[6-(p-cyanophenyl)-3-pyridazinyl]carbazate | 100 | 2 | 58 | 71 |
| Ethyl 3-[6-(p-bromophenyl)-3-pyridazinyl]carbazate | 100 | 1 | 69 | 67 |
| Ethyl 3-[5-methyl-6-(m-nitrophenyl)-3-pyridazinyl]carbazate | 100 | 1 | 64 | 68 |
| Ethyl 3-[6-(p-cyanophenyl)-5-methyl-3-pyridazinyl]carbazate | 100 | 2 | 57 | 62 |
| Ethyl 3-[6-(p-bromophenyl)-5-methyl-3-pyridazinyl]carbazate | 100 | 1 | 60 | — |
| Starch (vehicle) | — | 50 | 122 | — |
| | — | 50 | — | 118 |

The preceding test was repeated in essentially the same manner using spontaneously hypertensive Taconic Farms rats and dosing the animals twice at a 24 hour interval.

The results of this test with representative compounds of this invention appear in Table II.

The invention will be described in greater detail in conjunction with the following specific examples.

EXAMPLE 1

Preparation of Intermediate
6-(p-Cyanophenyl)-3-chloropyridazine

Table II

| COMPOUND | DOSE (mg/Kg) | NO. OF RATS | MEAN ARTERIAL BLOOD PRESSURE (mm Hg) 28 HOURS AFTER 1st DOSE 4 HOURS AFTER 2nd DOSE |
|---|---|---|---|
| Ethyl 3-[6-(p-chlorophenyl)-3-pyridazinyl]carbazate | 100 | 2 | 80 |
| t-Butyl 3-[6-(p-cyanophenyl)-5-methyl]-3-pyridazinyl]carbazate | 100 | 2 | 90 |
| Ethyl 3-[6-(m-cyanophenyl)-5-methyl-3-pyridazinyl]carbazate | 100 | 2 | 85 |
| Ethyl 3-(6-phenyl-5-methyl-3-pyridazinyl)carbazate | 100 | 2 | 83 |
| Starch (vehicle) | — | 2 | 162 |

The novel carbazates of this invention are useful as anti-hypertension agents in mammals when administered in amounts ranging from about 0.5 mg. per kg. to about 40 mg. per kg. of body weight per day. A preferred dosage regimen for optimum results would be from about 2 mg. per kg. to about 29 mg. per kg. Thus the daily dosage employed for a subject of about 70 kg.

A mixture of 86.3 g of 6-(p-bromophenyl)-4,5-dihydro-3(2H)-pyridazinone (prepared as described in Example 5 of U.S. Pat. No. 3,689,652) in 500 ml. of glacial acetic acid is heated to 80° C. with continuous stirring. A solution of 60 g. (19.2 ml) of bromine in 80 ml. of acetic acid is added dropwise at 75°-80° C. over a period of 1 hour. The mixture is heated with stirring on a steam bath for ½ hour more and then poured into 3 liters of cracked ice and water. The white solid is collected by filtration and air dried, yielding 6-(p-bromophenyl)-3(2H)-pyridazinone.

A 19.20 g. portion of 6-(p-bromophenyl)-3(2H)-pyridazinone is mixed with 9.10 g. of cuprous cyanide in 70 ml. of dimethylformamide and stirred at reflux temperature for 12 hours. The hot mixture is poured into a solution of 46 ml. of ethylenediamine in 230 ml. of water. The mixture is stirred at ice-bath temperature for 30 minutes and the solid is separated by filtration. A second crop forms in the filtrate which is collected and added to the first crop which is then washed with water yielding 6-(p-cyanophenyl)-3(2H)-pyridazinone.

A 3.42 g. portion of 6-(p-cyanophenyl)-3(2H)-pyridazinone in 25 ml. of phosphorus oxychloride is stirred and heated at reflux temperature for 3 hours. Most of the excess phosphorus oxychloride is removed under reduced pressure. Cracked ice-water is added to the concentrate which is stirred until the excess phosphorus oxychloride hydrolyzes. The solid is collected by filtration, dried and recrystallized from dimethylformamide-water, yielding 6-(p-cyanophenyl)-3-chloropyridazine, m.p. 236°–238° C.

EXAMPLE 2

Ethyl 3-[6-(p-cyanophenyl)-3-pyridazinyl]carbazate

A mixture of 0.40 g. of 6-(p-cyanophenyl)-3-chloropyridazine and 0.70 g. of 97% ethyl carbazate in 25 ml. of n-butanol is prepared. The solution is stirred and heated at reflux temperature for 4 hours. The reaction mixture is cooled to room temperature and the product precipitated from solution. The product is filtered, washed with n-butanol, water, dried and recrystallized from ethanol giving a crystalline material, m.p. 235° C.

EXAMPLE 3

Preparation of Intermediate
6-(p-bromophenyl)-3-chloropyridazine

A mixture of 20.0 g. of 6-(p-bromophenyl)-3(2H)-pyridazinone (prepared as described in Example 1) in 100 ml. of phosphorus oxychloride is heated at reflux temperature for 4½ hours. The excess phosphorus oxychloride is removed under reduced pressure and the residue is stirred with water-cracked ice to decompose the remaining phosphorus oxychloride. The product is recovered by filtration and recrystallized from dilute dimethylformamide yielding tan crystals, m.p. 201°–203° C.

EXAMPLE 4

Ethyl 3-[6-(p-bromophenyl)-3-pyridazinyl]carbazate

A mixture of 2.69 g. of 6-(p-bromophenyl)-3-chloropyridazine and 3.12 g. of ethyl carbazate in 50 ml. of n-butyl alcohol is prepared. This solution is stirred and heated at reflux temperature for 4 hours. The reaction mixture is cooled to room temperature and the solvent removed on a rotation evaporator. The residue is triturated with water and the resulting solid collected by filtration. The product is recrystallized from ethanol to give crystalline material, m.p. 190°–192° C.

EXAMPLE 5

Preparation of Intermediate
6-(p-chlorophenyl)-3-chloropyridazine

A 283 g. portion of 6-(p-chlorophenyl)-4,5-dihydro-3(2H)-pyridazinone (prepared as described in Example 1 of U.S. Pat. No. 3,689,652) is suspended in 2500 ml. of acetic acid at room temperature with stirring. A 227 g. (72.7 ml.) portion of bromine is dissolved in 300 ml. of acetic acid and 20% of this solution is added to the reaction mixture which is then heated on a steam bath until the bromine color disappears. The balance of the bromine solution is added portionwise, over a ½ hour period to the heated solution. The reaction mixture is heated for an additional hour and then poured into crushed ice. The resulting solid is recovered by filtration, washed with water and dried yielding an off-white solid, m.p. 269°–272° C., 6-(p-chlorophenyl)-3(2H)-pyridazinone.

A 269 g. portion of 6-(p-chlorophenyl)-3(2H)-pyridazinone and 1500 ml. of phosphorus oxychloride are heated on a steam bath for 5 hours. The excess phosphorus oxychloride is removed under vacuum. The solid concentrate is diluted with ice water and the resulting solid is recovered by filtration, washed with water and dried. This product is recrystallized twice from dimethylformamide-water yielding 6-(p-chlorophenyl)-3-chloropyridazine as an off-white solid, m.p. 202°–204° C.

EXAMPLE 6

Ethyl 3-[6-(p-chlorophenyl)-3-pyridazinyl]carbazate

A mixture of 5.0 g. of 6-(p-chlorophenyl)-3-chloropyridazine and 6.86 g. of ethyl carbazate in 80 ml. of n-butyl alcohol is prepared. This solution is stirred and heated at reflux temperature for 4 hours. The reaction mixture is cooled in an ice bath and the resulting solid filtered, washed with n-butyl alcohol, water and dried. The product is recrystallized from ethanol to give crystalline material, m.p. 190°–192° C.

EXAMPLE 7

Ethyl 3-[6-(p-chlorophenyl)-3-pyridazinyl]carbazate

A mixture of 10.0 g. of 6-(p-chlorophenyl)-3-chloropyridazine, 6.6 g. of hydrazine hydrate and 150 ml. of butanol is heated at reflux overnight. The reaction mixture is cooled and the precipitate is collected by filtration, washed with butanol and water and then dried yielding 6-(p-chlorophenyl)-3-hydrazinopyridazine.

A mixture of 1.0 g. of 6-(p-chlorophenyl)-3-hydrazinopyridazine and 0.65 g. of diisopropylethylamine in 25 ml. of dioxane are placed in a flask and warmed slightly. To this is added 0.5 g. (0.45 ml.) of ethyl chloroformate and the reaction is stirred for one hour. The dioxane is removed on a rotating evaporator and ethanol is added to the residue resulting in a precipitate. This precipitate is recrystallized from ethanol giving a yellow solid, m.p. 176°–180° C.

EXAMPLE 8

Preparation of Intermediate
5-methyl-6-(m-nitrophenyl)-3-chloropyridazine

A 24.9 g. portion of 4,5-dihydro-5-methyl-6-(m-nitrophenyl)-3(2H)-pyridazinone (prepared as described in Example 9 of U.S. Pat. No. 3,822,260) is dissolved in 200 ml. of warm stirred acetic acid. A 19.2 g. (6.2 ml.) portion of bromine, dissolved in 50 ml. of acetic acid is added dropwise over a 15 minute period. After an additional 20 minutes of warming to expel the HBr, the reaction mixture is poured into crushed ice. The resulting solid is recovered by filtration and washed with large amounts of water. The solid is dried yielding 5-methyl-6-(m-nitrophenyl)-3(2H)-pyridazinone as a cream colored solid.

A 22.7 g. portion of 5-methyl-6-(m-nitrophenyl)-3(2H)-pyridazinone in 230 ml. of phosphorus oxychloride is heated on a steam bath for 3 hours. The reaction mixture is poured portionwise into crushed ice with stirring. The resulting solid is collected by filtration, washed with water and then dried yielding 5-methyl-6-(m-nitrophenyl)-3-chloropyridazine, m.p. 169°–171° C.

EXAMPLE 9

Ethyl 3-[6-(m-nitrophenyl)-5-methyl-3-pyridazinyl]carbazate

A 2.49 g. portion of 6-(m-nitrophenyl)-5-methyl-3-chloropyridazine and 2.18 g. of ethyl carbazate in 50 ml. of butyl alcohol are stirred at reflux for 4 hours. The reaction mixture is concentrated free of solvent and the concentrate is shaken with ether and water. The resulting solid is recovered by filtration, washed with water and ether and dried, yielding ethyl 3-[6-(m-nitrophenyl)-5-methyl-3-pyridazinyl]carbazate as a cream colored solid, m.p. 186°–187° C.

EXAMPLE 10

Preparation of Intermediate 6-(p-cyanophenyl)-5-methyl-3-chloropyridazine

A 5.0 g. portion of 6-(p-cyanophenyl)-4,5-dihydro-5-methyl-3(2H)-pyridazinone (prepared as described in Example 44 of U.S. Pat. No. 3,824,271) is slurried in 25 ml. of acetic acid. A solution of 1.4 ml. of bromine in 25 ml. of acetic acid is added and the reaction mixture is heated on a steam bath for 30 minutes. A 400 ml. portion of ice water is added and the resulting solid is collected by filtration. This product is heated in 200 ml. of a mixture of ethyl acetate and methanol at the boiling point and filtered free of insolubles. The filtrate is concentrated to about 75 ml., cooled in ice and the resulting white solid collected and dried, yielding 6-(p-cyanophenyl)-5-methyl-3(2H)-pyridazinone.

A 2.0 portion of 6-(p-cyanophenyl)-5-methyl-3(2H)-pyridazinone and 10 ml. of phosphorus oxychloride are heated at steam bath temperature for 4 hours. The reaction mixture is poured into crushed ice and the resulting solid, after decomposition of the unreacted phosphorus oxychloride, is recovered by filtration, washed with water and dried. This product is recrystallized several times from methanol giving 6-(p-cyanophenyl)-5-methyl-3-chloropyridazine, m.p. 218°–220° C.

EXAMPLE 11

Ethyl 3-[6-(p-cyanophenyl)-5-methyl-3-pyridazinyl]carbazate

A mixture of 2.29 g. of 6-(p-cyanophenyl)-5-methyl-3-chloropyridazine and 2.18 g. of ethyl carbazate in 50 ml. of n-butyl alcohol is prepared. This solution is stirred and heated at reflux temperature for 4 hours. The reaction mixture is cooled to room temperature and the solvent removed on a rotating evaporator. Water is added to the residue and the resulting solid filtered, washed with water, ether and dried. The product is recrystallized from ethanol, m.p. 189°–191° C.

EXAMPLE 12

Preparation of Intermediate 6-(p-Bromophenyl)-5-methyl-3-chloropyridazine

A 2.67 g. portion of 6-(p-bromophenyl)-4,5-dihydro-5-methyl-3(2H)-pyridazinone (prepared as described in Example 38 of U.S. Pat. No. 3,824,271) is suspended in 20 ml. of acetic acid. A 1.91 g. (0.62 ml.) portion of bromine in 5 ml. of acetic acid is added dropwise, while the reaction mixture is heated on a steam bath. Heating is continued for an additional 30 minutes. The reaction mixture is poured into crushed ice. The resulting solid is recovered by filtration, washed with water and dried, yielding 6-(p-bromophenyl)-5-methyl-3(2H)-pyridazinone.

A 2.0 g. portion of 6-(p-bromophenyl)-5-methyl-3(2H)-pyridazinone and 20 ml. of phosphorus oxychloride are heated on a steam bath for 3 hours. The reaction mixture is poured slowly into crushed ice. The excess phosphorus oxychloride is decomposed. The solid which forms is recovered by filtration, washed with water, dried and recrystallized twice from chloroform, yielding 6-(p-bromophenyl)-5-methyl-3-chloropyridazine, m.p. 197°–200° C.

EXAMPLE 13

Ethyl 3-[6-(p-bromophenyl)-5-methyl-3-pyridazinyl]carbazate

A mixture of 8.49 g. of 6-(p-bromophenyl)-5-methyl-3-chloropyridazine and 6.25 g. of ethyl carbazate in 100 ml. of n-butyl alcohol is prepared. This solution is stirred and heated at reflux temperature for 4 hours. The reaction mixture is cooled to room temperature and the solvent removed on a rotating evaporator. Water is added to the residue and the resulting solid filtered, washed with water, ether and dried. The product is recrystallized from ethanol to yield the product, m.p. 178°–179° C.

EXAMPLE 14

Preparation of Intermediate 6-phenyl-3-(1-methylhydrazino)pyridazine

A mixture of 10.0 g. of 6-phenyl-3-chloropyridazine 7.8 g. of methylhydrazine and 75 ml. of n-butanol is refluxed 6 hours. The mixture is cooled and filtered to give product and the filtrate is concentrated and filtered to give additional product. The two crops of product are recrystallized from ethanol to give crystals, m.p. 145°–147° C.

EXAMPLE 15

Ethyl 3-[6-(phenyl)-3-pyridazinyl]-3-methylcarbazate

A solution of 4.4 g. of 6-phenyl-3-(1-methylhydrazino)pyridazine, 3.4 g. of N,N-diisopropylethylamine and 50 ml. of dixane is prepared. To the solution is added 2.6 g. of ethyl chloroformate and the mixture is stirred for 2 hours. The solvent is removed under vacuum and to the residue is added ethanol and water. Filtration gives the product which is recrystallized from ethanol to give crystals, m.p. 129°–130° C.

EXAMPLE 16

Conversion of Ethyl 3-[6-(m-nitrophenyl)-5-methyl-3-pyridazinyl]carbazate to Ethyl 3-[6-(m-aminophenyl)-5-methyl-3-pyridazinyl]carbazate A 2.0 g. portion of ethyl 3-[6-(m-nitrophenyl)-5-methyl-3-pyridazinyl]carbazate and a catalytic amount of 10% palladium on carbon catalyst in 100 ml. of ethanol are reacted in 100 ml. of ethanol under 40 lb. of hydrogen pressure for 3 hours while the reaction vessel is heated with a jacketed heater. The reaction mixture is filtered free of catalyst and the filtrate is concentrated to an oil which is triturated with a mixture of ether and petroleum ether. The product is recrystallized from methanol after clarification through activated carbon to yield off-white crystals, m.p. 174°–175° C.

EXAMPLE 17

Preparation of Intermediate 5-methyl-6-phenyl-3-chloropyridazine

A 10.0 g. portion of 5-methyl-6-p-bromophenyl-3(2H)-pyridazinone and 1.0 g. of 10% palladium on carbon catalyst in 150 ml. of ethanol and 50 ml. of ammonium hydroxide is shaken under 40 lb. of hydrogen pressure for 4 hours in a Parr bottle, heated to 50° C. with an outside jacket. The reaction mixture is suction filtered and the filtrate concentrated to a white solid which is washed with water and air dried to afford 5-methyl-6-phenyl-3(2H)-pyridazinone as white crystals.

A 24.4 g. portion of 5-methyl-6-phenyl-3(2H)-pyridazinone (prepared as described above) and 250 ml. of phosphorus oxychloride are heated on a steam bath for 6 hours. The reaction mixture is concentrated free of phosphorus oxychloride in vacuo and the concentrate is triturated with cold water. The resulting solid is filtered, washed with water, recrystallized twice from methanol and dried giving a white solid, m.p. 125°–126° C.

EXAMPLE 18

Ethyl 3-(5-methyl-6-phenyl-3-pyridazinyl)carbazate

A 10.0 g. portion of 5-methyl-6-phenyl-3-chloropyridazine, 10.02 g. of ethyl carbazate and 150 ml. of butyl alcohol are stirred at reflux for 4 hours. The reaction mixture is concentrated free of butyl alcohol and the concentrate is placed in cold water containing a small amount of ethyl and scratched. The resulting solid is filtered, washed with water, recrystallized from a mixture of chloroform and petroleum ether and dried in vacuo giving a white solid, mp 143°–145° C.

EXAMPLE 19

Ethyl 3-(5-methyl-6-phenyl-3-pyridazinyl)carbazate

A 4.0 g. portion of ethyl 3-[6-(p-bromophenyl)-5-methyl-3-pyridazinyl]carbazate and 0.9 g. of 10% palladium on carbon catalyst in 100 ml. of ethanol and 50 ml. of ammonium hydroxide is shaken under 40 lb. of hydrogen pressure for 4 hours with external heating of the bottle by means of a heated jacket. The reaction mixture is suction filtered and the filtrate is concentrated to a light yellow oil which is scratched with petroleum ether to give a white solid, m.p. 142°–145° C.

EXAMPLE 20 t-Butyl 3-[6-(p-cyanophenyl)-5-methyl-3-pyridazinyl]carbazate

A mixture of 5.0 g. of 6-(p-cyanophenyl)-3-chloropyridazine, 8.71 g. of t-butylcarbazate and 100 ml. of butanol are heated at reflux for 3 hours. The solvent is removed on a rotating evaporator. Water is added, the resulting product is recovered by filtration, washed with water, recrystallized from methanol and dried yielding a product having a m.p. 169°–171° C.

EXAMPLE 21

Ethyl 3-methyl-3-[6-(p-chlorophenyl)-3-pyridazinyl]carbazate

A 10.0 g. portion of 6-(p-chlorophenyl)-3-chloropyridazine and 6.1 g. of methyl hydrazine in 125 ml. of butanol is mixed and heated at reflux overnight. The reaction mixture is cooled, filtered, the precipitate is washed with butanol and water and dried. Recrystallization from ethanol gives 6-(p-chlorophenyl)-3-(1-methylhydrazino)pyridazine.

A 2.0 g. portion of 6-(p-chlorophenyl)-3-(1-methylhydrazino)pyridazine and 1.30 g. of diisopropylethylamine in 50 ml. of dioxane is warmed slightly in a flask. A 1.0 g. portion of ethyl chloroformate is added and the reaction mixture is stirred for one hour. The dioxane is removed on a rotary evaporator, ethanol and water are added to the residue and a precipitate results. The solid is recrystallized from ethanol to give a pure white solid, m.p. 170°–172° C.

EXAMPLE 22

Preparation of Intermediate 6-(m-cyanophenyl)-5-methyl-3-chloropyridazine

A 2.95 g. portion of 6-(m-cyanophenyl)-5-methyl-3(2H)-pyridazinone [prepared as described in Example 8 but employing 4,5-dihydro-5-methyl-6-(m-cyanophenyl)-3(2H)-pyridazinone (which in turn is prepared by employing 6-(m-chlorophenyl)-4,5-dihydro-5-methyl-3(2H)-pyridazinone in Example 44 of U.S. Pat. No. 3,824,271)] and 35 ml. of phosphorus oxychloride are heated on a steam bath for 5 hours. The mixture is concentrated free of excess phosphorus oxychloride and the concentrate is diluted with ice water. The resulting product, a tan solid, is recovered by filtration, washed with water and dried, m.p. 153°–155° C.

EXAMPLE 23

Ethyl 3-[6-(m-cyanophenyl)-5-methyl-3-pyridazinyl]carbazate

A 3.15 g. portion of 6-(m-cyanophenyl)-5-methyl-3-chloropyridazine and 2.85 g. of ethyl carbazate in 50 ml. of butanol is stirred at reflux temperature for 4 hours. The mixture is concentrated free of solvent and the oily concentrate is triturated with water and a little ether. The resulting solid is recovered by filtration, air dried and recrystallized several times from ethanol giving a white solid, m.p. 189°–190° C.

EXAMPLE 24 t-Butyl-3-[5-methyl-6-(m-nitrophenyl)-3-pyridazinyl]carbazate

A mixture of 5.49 g. of 5-methyl-6-(m-nitrophenyl)-3-chloropyridazine and 8.71 g. of t-butylcarbazate in 100 ml. of butanol is heated at reflux for 3 hours and then allowed to cool to room temperature overnight. The butanol is removed on a rotating evaporator leaving a heavy liquid residue. The final product is obtained after crystallization from a minimum amount of methanol on standing, washing with methanol, water and drying, m.p. 160°–162° C.

EXAMPLE 25

Preparation of Intermediate 5-methyl-3-(m-nitrophenyl)-6-(1-methylhydrazino)-pyridazine To an 8.0 g. portion of 5-methyl-6-(m-nitrophenyl)-3-chloropyridazine in 100 ml. of butanol is added 4.4 g. of methyl hydrazine. This reaction mixture is heated at reflux overnight and then cooled in an ice bath. The product which forms as a precipitate is collected by filtration, washed with butanol, water, dried and recrystallized from ethanol, m.p. 173°–174° C.

EXAMPLE 26

Ethyl 3-methyl-3-[5-methyl-6-(m-nitrophenyl)-3-pyridazinyl]-carbazate

A mixture of 1.6 g. of 5-methyl-3-(m-nitrophenyl)-6-(1-methylhydrazino)pyridazine, 1.03 g. of diisopropylethylamine and 40 ml. of dioxane in a 100 ml. round bottom flask is warmed slightly until solution takes place. A 0.75 g. portion of ethyl chloroformate is pipetted into the solution for one hour and then the dioxane is removed on a rotating evaporator. The product is obtained after recrystallization from acetone-petroleum ether, m.p. 142°–144° C.

EXAMPLE 27

2-{1-[6-(p-chlorophenyl)-3-pyridazinyl]hydrazino}ethanol

A mixture of 5.0 g. of 6-(p-chlorophenyl)-3-chloropyridazine and 5.02 g. of 2-hydroxyethylhydrazine in 75 ml. of butanol is heated at reflux overnight and then cooled in an ice bath. The precipitate is collected by filtration, washed with butanol, water and then dried. Recrystallization from ethanol gives crystals, m.p. 172°–174° C.

EXAMPLE 28

Ethyl 3-[5,6-bis(p-methoxyphenyl)-3-pyridazinyl]carbazate

A mixture of 5.0 g. of 5,6-bis(p-methoxyphenyl)-3-chloropyridazine, 3.64 g. of ethyl carbazate and 60 ml. of n-butanol is refluxed for 2.5 hours. The solvent is removed under vacuum and the residue tritrated with water. Filtration gives the product as crystals. Recrystallization from ethanol gives ethyl 3-[5,6-bis(p-methoxyphenyl)-3-pyridazinyl]carbazate as crystals, m.p. 212°–214° C.

EXAMPLE 29

Ethyl 3-(6-phenyl-3-pyridazinyl)carbazate

A mixture of 15.0 g. of 6-phenyl-3-chloropyridazine, 16.3 g. of ethyl carbazate, and 250 ml. of n-butanol is refluxed for 3 hours. The solvent is removed under vacuum and the residue triturated with cold water. Filtration gives 18.6 g. of cream colored crystals. Recrystallization gives white crystals, m.p. 158°–160° C.

EXAMPLE 30

Ethyl 3-(6-phenyl-3-pyridazinyl)carbazate

A mixture of 15.57 g. of ethyl 3-[6-(p-bromophenyl)-3-pyridazinyl]carbazate, 1.5 g. of 10% palladium on carbon catalyst, 200 ml. of ethanol and 60 ml. of ammonium hydroxide is shaken under 40 lb. of hydrogen pressure for 4 hours with external heating of bottle by means of a heated jacket. The reaction mixture is filtered and the filtrate concentrated to a solid which is washed with water to give 10.1 g. of cream colored crystals. Recrystallization by dissolving in ethanol and diluting with petroleum ether gave white crystals, m.p. 158°–160° C.

EXAMPLE 31

Ethyl 3-[6-(m-cyanophenyl)-5-methyl-3-pyridazinyl]carbazate

A solution of 2.87 g. of ethyl 3-[6-(m-aminophenyl)-5-methyl-3-pyridazinyl]carbazate, 80 ml. of water, 10 ml. of concentrated hydrochloric acid is stirred at 0° and a solution of 0.76 g. of sodium nitrite in 10 ml. of water added dropwise over 10 minutes. After stirring for 15 minutes, the cold solution is added dropwise to a cold solution of 2.5 g. of cuprous cyanide, 2.27 g. of potassium cyanide, 50 ml. of water and 35 ml. of toluene. After stirring at 0° for 1 hour and at room temperature overnight, the mixture is filtered and the solid washed with water to give 4.3 g. of gray crystals. Purification gives product as crystals, m.p. 189°–190° C.

EXAMPLE 32

Methyl 3-[6-(p-cyanophenyl)-5-methyl-3-pyridazinyl]carbazate

A mixture of 18.0 g. of 6-(p-cyanophenyl)-5-methyl-3-chloropyridazine, 13.3 g. of methyl carbazate and 200 ml. of n-butanol is refluxed for 3 hours. The solvent is removed to give an oil which crystallizes on addition of water to give 11.9 g. of product. Recrystallization from methanol-ether gives white crystals, m.p. 191°–192° C.

EXAMPLE 33

Methyl 3-[6-(m-nitrophenyl)-5-methyl-3-pyridazinyl]carbazate

A mixture of 11.4 g. of 6-(m-nitrophenyl)-3-chloropyridazine, 8.25 g. of methyl carbazate and 150 ml. of n-butanol is refluxed for 3 hours. The solvent is removed and the oily redisue stirred with cold water. The solid is filtered to give 11.5 g. of crystals which are recrystallized from methanol-petroleum ether to give off-white crystals, m.p. 198°–199° C.

EXAMPLE 34

Ethyl 3-[6-(p-fluorophenyl)-3-pyridazinyl]carbazate

A mixture of 5.0 g. of 6-(p-fluorophenyl)-3-chloropyridazine, 5.0 g. of ethyl carbazate and 50 ml. of n-butanol is refluxed for 2 hours. The solvent is removed and the residue washed with water and recrystallized from ethanol to give 1.75 g. of 3-[6-(p-fluorophenyl)-3-pyridazinyl]carbazate as crystals, m.p. 173°–174° C.

EXAMPLE 35

Ethyl 3-[6-(p-chlorophenyl)-3-pyridazinyl]-3-(2-hydroxyethyl)carbazate

To a mixture of 0.60 g. of 2- 1-[6-(p-chlorphenyl)-3-pyridazinyl]hydrazino ethanol, 0.30 g. of N,N-diisopropylethylamine and 25 ml. of dioxane is added 0.25 g. of ethyl chloroformate. The mixture is stirred for 1 hour and the solvent removed. Water is added and the solid which separates is filtered, washed with water and recrystallized from ethanol-ether to give product as crystals, m.p. 152°–154° C.

EXAMPLE 36

Preparation of intermediate 6-($\alpha,\alpha,\alpha$-trifluoro-m-tolyl)-3-chloropyridazine To a solution of 112 g of p-toluenesulfonic acid in 500 ml. of tetrahydrofuran is added portionwise 106 g. of morpholine. After stirring and refluxing for 2 hours, the mixture is cooled (ice-bath) and 42.2 g of potassium cyanide in 75 ml. of water is added. The mixture is refluxed over night and the solvent is removed under reduced pressure. The residue is partitioned between water and chloroform and the chloroform layer separated, washed with saturated sodium bisulfite and dried (MgSO$_4$). Removal of the solvent under vacuum gives 152 g. of product as a yellow oil. A sample is chromatographed over silica gel with chloroform as eluent to give $\alpha$-($\alpha,\alpha,\alpha$-trifluoro-m-tolyl)-4-morpholineacetonitrite as a yellow oil.

A 5.0 g. sample of $\alpha$-($\alpha,\alpha,\alpha$-trifluoro-m-tolyl)-4-morpholineacetonitrile is dissolved in 200 ml. of tetrahydrofuran and 30 drops of solution containing 30% potassium hydroxide in ethanol is added. Ethyl acrylate (10 ml.) is added and the mixture is stirred for 1 hour. Another 30 drops of solution containing 30% potassium hydroxide in ethanol is added and another 10 ml. of ethyl acrylate. After stirring 2 hours, the solvent is concentrated free of solvent under reduced pressure. Toluene is added several times and the solven removed after each addition. Ether is added and the mixture is filtered. Concentration under vacuum gives the product as a yellow oil (5.6 g.). Chromatography over silica gel with solvent chloroform gives 4.8 g. of ethyl $\gamma$-cyano-$\gamma$-($\alpha,\alpha,\alpha$-trifluoro-m-tolyl)-4-morpholinebutyrate as a yellow oil.

A mixture of 2.05 g. of ethyl $\gamma$-cyano-$\gamma$-($\alpha,\alpha,\alpha$-trifluoro-m-tolyl)-4-morpholinebutyrate and 0.3 g. of hydrazine hydrate in 100 ml. of ethanol is refluxed overnight. The solvent is removed under vacuum and the residue stirred with petroleum ether. Filtration gives the product as white crystals, m.p. 168°–170° C. Recrystallization from chloroform-petroleum ether gives 4,5-dihydro-6-($\alpha,\alpha,\alpha$-trifluoro-m-tolyl)-3-(2H)-pyridazinone as white crystals, m.p. 170°–171° C.

A solution of 4,5-dihydro-6-($\alpha,\alpha,\alpha$-trifluor-m-tolyl)-3-pyridazinone in 45 ml. of glacid acetic acid is prepared. To the solution is added 2.5 ml. of glacial acetic acid containing 0.68 g. of bromine. The mixture is heated on a steam bath until the bromine color disappears. Then an additional 2.5 ml. of glacial acetic acid containing 0.68 g. of bromine is added and the heating is continued for 10 minutes. The mixture is concentrated under reduced pressure and ice water added to the residue. The resulting solid is filtered and washed with water to give white crystals, m.p. 211°–214° C. Recrystallization of a sample gives 6-($\alpha,\alpha,\alpha$-trifluror-m-tolyl)-3(2H)-pyridazinone as white crystals, m.p. 215°–218° C.

A mixture of 12.6 g. of 6-($\alpha,\alpha,\alpha$-trifluoro-m-tolyl)-3(2H)-pyridazinone and 200 ml. of phosphorus oxychloride is heated on a steam bath for 18 hours. The mixture is concentrated under vacuum and the residue triturated with cold water. The resulting solid is washed with water and air dried to give 13.5 g. of cream colored crystals, m.p. 131°–133° C. Recrystallization from methanol gives 6-($\alpha,\alpha,\alpha$-trifluoro-m-tolyl)-3-chloropyridazine as white crystals, m.p. 131°–133° C.

EXAMPLE 37

Ethyl 3-[6-($\alpha,\alpha,\alpha$-trifluoro-m-tolyl)-3-pyridazinyl]carbazate

A mixture of 3.0 g. of 6-($\alpha,\alpha,\alpha$-trifluoro-m-tolyl)-3-chloropyridazine, 2.5 g. of ethyl carbazate and 50 ml. of n-butanol is refluxed for 4 hours. The solvent is removed under vacuum and the residue stirred with cold water. Filtration gives 3.65 g. of ethyl 3-[6-($\alpha,\alpha,\alpha$-trifluoro-m-tolyl)-3-pyridazinyl]carbazate as cream colored crystals. Recrystallization from ethyl acetate-petroleum ether gives pale yellow crystals, m.p. 168°–170° C.

EXAMPLE 38

Ethyl-3-[6-(p-carboxamidophenyl)-5-methyl-3-pyridazinyl]carbazate

To 10 ml. of concentrated sulfuric acid cooled in an ice bath, is added 1.0 g. of ethyl 3-[6-(p-cyanophenyl)-5-methyl-3-pyridazinyl]carbazate. The mixture is stirred for ¼ hour and allowed to stand at room temperature overnight. The cold mixture is made alkaline with 5N sodium hydroxide and the solid which separates is filtered to give 0.83 g. of tan solid.

EXAMPLE 39

Preparation of intermediate 6-(p-cyanophenyl)-5-methyl-3-(1-methylhydrazino)-pyridazine A mixture of 7.5 g. of 6-(p-cyanophenyl)-3-chloropyridazine, 3.5 g. of methylhydrazine and 75 ml. of n-butanol is refluxed for 3 hours. The mixture is cooled and filtered to give the product. Recrystallization from dioxane gives 6-(p-cyanophenyl)-5-methyl-3-(1-methylhydrazino)pyridazine as tan crystals, m.p. 149°–152° C.

EXAMPLE 40

Ethyl 3-[6-(p-cyanophenyl)-5-methyl-3-pyridazinyl]-3-methylcarbazate

A solution of 2.86 g. of 6-(p-cyanophenyl)-5-methyl-3-pyridazinyl]-3-(1-methylhydrazino)pyridazine, 2.1 g. of N,N-diisopropylethylamine in 70 ml. of dioxane is prepared. To the solution is added 1.50 g. of ethyl chloroformate. After stirring for 1 hour the solvent is removed under vacuum and the residue dissolved in ethanol. On standing the product crystallizes and is recrystallized from acetone-petroleum ether to give crystals, m.p. 138°–142° C.

EXAMPLE 41

Ethyl-3-[6-(p-cyanophenyl)-5-methyl-3-pyridazinyl]-3-methylcarbazate hydrochloride In a similar run the hydrochloride of ethyl 3-[6-(p-cyanophenyl)-5-methyl-3-pyridazinyl]-3-methylcarbazate is isolated when the residue is chromatographed over silica gel to give product, m.p. 241°–244° C.

EXAMPLE 42

Preparation of intermediate 6-(p-fluorophenyl)-3-(1-methylhydazino)pyridazine

A mixture of 7.5 g. of 6-(p-fluorophenyl)-3-chloropyridazine, 5.0 g. of methylhydrazine and 50 ml. of n-butanol is refluxed for 4 hours. The mixture is cooled and filtered to give the product. Recrystallization from ethanol gives product as crystals, m.p. 170°–172° C.

EXAMPLE 43

Ethyl 3-[6-(p-fluorophenyl)-3-pyridazinyl]-3-methylcarbazate

A solution of 2.7 g. of 6-(p-fluorophenyl)-3-(1-methylhydrazino)pyridazine, 1.94 g. of N,N-diisopropylethylamine and 60 ml. of dioxane is prepared. To the solution is added 1.50 g. of ethyl chloroformate and the mixture is stirred for 2 hours. The solvent is removed under vacuum and to the residue is added ethanol and water. Filtration gives the product which is recrystallized from ethanol to give crystals, m.p. 160°–161° C.

We claim:

1. A compound of the formula:

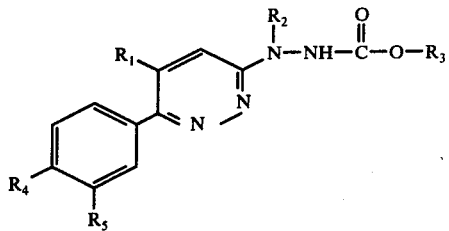

wherein $R_1$, $R_2$ and $R_3$ are each individually selected from the group consisting of hydrogen and alkyl having from 1 to 4 carbon atoms and $R_4$ and $R_5$ are each individually selected from the group consisting of hydrogen, fluoro, chloro, bromo, cyano, methoxy, nitro, amino, trifluoromethyl and carbamoyl with the proviso that at least one of $R_4$ and $R_5$ is hydrogen.

2. The compound according to claim 1, ethyl 3-[6-(p-cyanophenyl)-3-pyridazinyl]carbazate.

3. The compound according to claim 1, ethyl 3-[6-(p-cyanophenyl)-5-methyl-3-pyridazinyl]carbazate.

4. The compound according to claim 1, ethyl-3-[6-(m-cyanophenyl)-5-methyl-3-pyridazinyl]carbazate.

5. The compound according to claim 1, t-butyl 3-[6-(p-cyanophenyl)-5-methyl-3-pyridazinyl]carbazate.

6. The compound according to claim 1, ethyl 3-[6-(3,4-dichlorophenyl)-3-pyridazinyl]carbazate.

7. The compound according to claim 1, ethyl 3-[6-(p-cyanophenyl)-5-methyl-3-pyridazinyl]-3-methylcarbazate.

8. The compound according to claim 1, ethyl 3-[6-(p-fluorophenyl)-3-pyridazinyl]-3-methylcarbazate.

9. The compound according to claim 1, ethyl 3-(6-phenyl-3-pyridazinyl]carbazate.

10. The compound according to claim 1, methyl 3-[6-(p-cyanophenyl)-5-methyl-3-pyridazinyl]carbazate.

11. The compound according to claim 1, ethyl 3-[6-(p-fluorophenyl)-3-pyridazinyl]carbazate.

* * * * *